(12) United States Patent
Suhm

(10) Patent No.: US 6,491,429 B1
(45) Date of Patent: Dec. 10, 2002

(54) METHOD OF AUTOMATIC GUIDING A C-ARM X-RAY DEVICE

(75) Inventor: Norbert Suhm, Weil-Haltingen (DE)

(73) Assignees: AO-Development Institute Davos, Davos (CH); Peter Messmer, Oberwil (CH); Pietro Regazzoni, Basel (CH); Paul Muller, Riehen (CH); Urs Bopp, Basel (CH)

( * ) Notice: Subject to any disclaimer, the term of this patent is extended or adjusted under 35 U.S.C. 154(b) by 0 days.

(21) Appl. No.: 09/658,428

(22) Filed: Sep. 8, 2000

(51) Int. Cl.[7] .............................................. A61B 6/08
(52) U.S. Cl. ...................... 378/205; 378/206; 378/197; 378/198
(58) Field of Search ................................ 378/205, 197, 378/206, 198, 196; 600/425, 426; 606/130

(56) References Cited

U.S. PATENT DOCUMENTS 5,772,594 A * 6/1998 Barrick ...................... 600/407
5,850,836 A * 12/1998 Steiger et al. ............ 128/653.1

* cited by examiner

Primary Examiner—Robert H. Kim
Assistant Examiner—Glen Kao
(74) Attorney, Agent, or Firm—Rankin, Hill, Porter & Clark LLP

(57) ABSTRACT

The method concerns automatic guiding a C-arm X-ray device equipped with a motorized exact positioning unit and essentially comprises the steps of:

Figure 1:
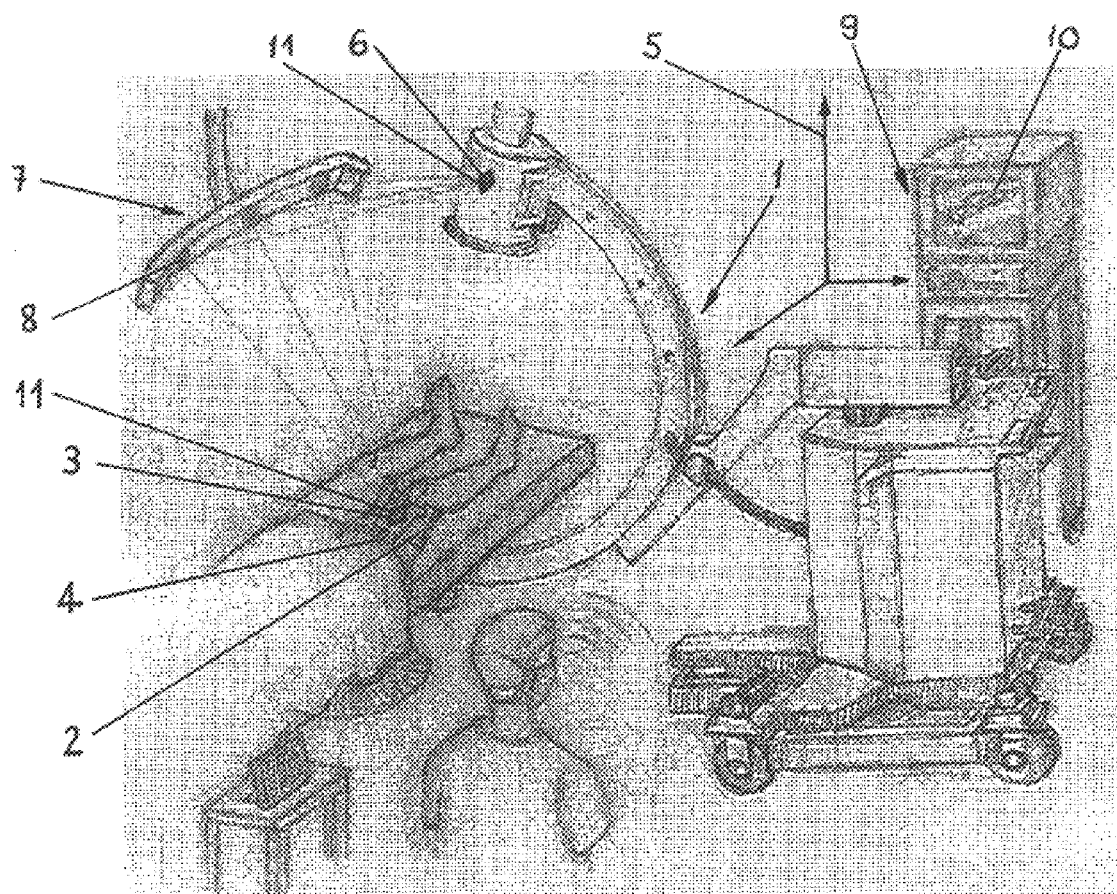

A) determining the position of the plane of projection (2);

E) measuring the position and orientation of the reference element (3) at the bone (4) or bone joint;

F) referencing the position of the plane of projection (2) to the position of the reference element (3);

H) measuring the actual position and orientation of the displaced bone (4);

I) determining the deviation between the actual position of the reference element (3) and the position of the reference element (3) as referenced under step F);

K) determining the new position of the C-arm X-ray device (1) in order to reset the plane of projection (2) as referenced under step F); and L) guiding the C-arm X-ray device (1) in the new position as determined under step K) by means of automatic controlling means.

9 Claims, 3 Drawing Sheets

METHOD OF AUTOMATIC GUIDING A C-ARM X-RAY DEVICE

The invention relates to a method of automatic guiding a C-arm X-ray device according to the concept of claim 1.

A C-arm X-ray device (in the following called C-arm) is used routinely today for the intraoperative control of length and axial and rotational alignment of bones or bone fragments in osteosynthesis. In order to point out the task of the method according to the invention the step "intraoperative imaging" is described as technical regulatory process in the following section.

In conventional, open operative technique the surgeon receives his visual feedback partly via direct vision without radiography. Therefore, a separate operative step 'intraoperative imaging' cannot be delineated. In order to obtain a particular view of a fracture, the surgeon may have to alter his own position relative to the patient or the position of the retractor on the patient. The desired view of the fracture corresponds to the target value and the patient can be identified as the controlled system. The surgeon records with his eye (measuring unit) the current view of the fracture and compares it with the desired view. From the difference (control deviation), the surgeon (controller) determines, on the basis of his experience, the type and extent of the necessary positional alteration. As a result the surgeon achieves a new view of the fracture which is expressed in regulatory terms as the actual value. In a block diagram, this situation may be expressed as a simple control circuit with only three elements. An optimal regulatory behavior is achieved on the basis of direct visual feedback and a simple control circuit. This model can be applied to the description of soft tissue interventions and of those open osteosynthesis procedures at which the C-arm is not used.

If the surgeon obtains his visual feedback by intraoperative imaging with the C-arm, then intraoperative imaging can be delineated as an individual operative stage. This will be expressed in the following as a technical regulatory process for the constellation intraoperative imaging with the C-arm and image guidance with the combination C-arm/ surgical navigation system.

Intraoperative imaging with the C-arm

For this constellation the external C-arm operator and the C-arm as a device must be taken into account as well as the patient and the surgeon in order to be expressed in regulatory terms. The representation in a block diagram therefore requires additional elements. The intraoperative positioning procedure can be described as a serial connection of one outer and one inner control circuit.

The outer control circuit includes all persons and appliances participating in the process, i.e. the surgeon, the C-arm operator, the patient, and the C-arm. Adjustment to the desired projection, in other words, the target value, is regulated by the outer control circuit. The current projection (actual value) is shown on the monitor of the image intensifier. The surgeon (controller) compares the desired and the current projection.

A projection is defined by the orientation of the rays relative to the object being imaged. For any desired projection, the C-arm must therefore take up a specific position relative to the imaged fragment. The surgeon can only tell his description of the desired position in somewhat inexact terms and this depends upon his experience (interpreter). He communicates the position to the C-arm operator. The operator of the C-arm, the patient and the C-arm correspond to the outer control circuit as the controlled system which the surgeon influences as controller.

On the other hand, the interaction between the operator of the C-arm, the patient and the C-arm can be described as a second, inner control circuit with which the correct position of the C-arm is achieved. The operator tries to move the C-arm to the position stipulated by the surgeon. The C-arm operator acts as a controller in that he compares the position stipulated by the surgeon (target value) with the existing position of the C-arm (actual value). On the basis of his experience (interpreter), he plans suitable corrective movements. These may or may not be possible due to circumstances such as limited space or concerns for sterility (=disturbance factors). The actual position is constantly registered by the C-arm operator by eye (measuring unit), i.e. he receives continuous direct visual feedback. Only when the operator is satisfied with the position of the C-arm and the regulatory process in the inner control circuit is completed does the surgeon receive his first, delayed, visual radiographic feedback (measuring unit C-arm). Before the desired projection appears on the screen, the above procedure may have to be repeated several times.

The entire process has to be repeated in the same manner in order to reproduce a projection.

Intraoperative imaging with the combination C-arm/Surgical Navigation System

Surgical navigation systems make possible continuous image guidance based on stored data. This is done by representing the spatial relationships between surgical instruments and anatomical objects of interest on the screen. A surgical navigation system includes a facility for recording the position of the instruments in the operation room as well as the software and corresponding hardware components. This operates on a transceiver principle: on each surgical instrument transmitters tuned to the receivers are permanently mounted. Their position in the operating theater tracked by the receiver and positional information transmitted to the navigation system. Before each application of the surgical navigation system digital images of the patient are copied from an imaging unit (CT, C-arm) to the navigation system. The positional data on surgical instruments and anatomical objects in the OR make it possible to generate a simulated projection of the current position of the instruments on the recorded digital images.

The combination of surgical navigation system and C-arm can be applied during trauma surgery in the modes "positioning of the C-arm" and "image guidance". In the "positioning" mode the navigation system helps the surgeon to place the C-arm correctly for a previously defined projection. To do this, the relative position of the C-arm with which the desired projection will be achieved and the object to be imaged (implant or fragment) are stored in the navigation system. Intraoperatively, the actual positions of C-arm and object to be imaged are tracked and from them the relative positions are calculated. Consequently, the target and the actual relative positions are imaged on the monitor of the navigation system.

To express this situation in terms of automated control engineering, the navigation system has to be taken into account. In the 'positioning' mode, it functions to set the target value for the surgeon. He can thus give more exact positional commands to the external operator of the C-arm. The navigation system is however not linked into the inner control circuit with which the positioning of the C-arm is controlled.

Even in this configuration the total process must be repeated as described if a previously set projection is to be reproduced.

In order to achieve an optimal handling procedure, the surgeon must be able to alter the position of the C-arm - and thus the visible image—independently and immediately. This requirement is not fulfilled if a C-arm is used with the usual equipment available today for intraoperative imaging: the device is operated and positioned by a third person. This procedure takes time, is open to error, and leads to additional difficulties:

The entire procedure for setting up a projection has to be repeated if the projection needs to be reproduced, for example, when checking a reduction manoeuvre.

The radiographic checks necessary for positioning represent an additional exposure to radiation for the patient and the team in the operation room.

The person operating the C-arm has to be available more or less throughout the operation even though assistance may only be required occasionally after long waits.

These problems show clearly that an improved interface between the surgeon and the imaging unit must be found for intraoperative imaging with the C-arm. This becomes even more apparent at image-guided operations in which the surgeon is almost totally dependent on the information from images for the coordination of his manipulations.

On this point, the invention intends to provide remedial measures. The invention is based on the objective of providing a method of using a C-arm X-ray device that is automatically guideable by means of automatic controlling means.

The invention solves the posed problem with a method that displays the features of claim 1.

To execute the method according to the invention the C-arm X-ray device must be equipped with a motorized positioning unit apt to adjust the C-arm X-ray device in a desired position upon receiving control commands given by the C-arm operator, the surgeon (e.g. "voice control") or by a computer assisted surgery system. Such a motorized exact positioning unit for a C-arm X-ray device (MEPUC) is disclosed in the International Patent Application No. PCT/CH00/00022.

The method according to the invention essentially comprises the steps of: A) attaching a first reference element at the bone or bone joint to be surgically treated in order to establish a measurable reference of the position and orientation of the bone or bone joint with respect to an on-site three-dimensional system of coordinates;

B) positioning the C-arm X-ray device in a desired position with a desired plane of projection at the bone or bone joint to be surgically treated. This first positioning may be effected manually through an assistant or by means of an control system which may be integrated in a Surgical navigation system;

C) measuring the position and orientation of a second reference element at the C-arm
X-ray device with respect to the on-site three-dimensional system of coordinates in order to determine the position of the C-arm X-ray device with respect to the on-site three-dimensional system of coordinates;

D) determining the position and orientation of the plane of projection with respect to the on-site systems of coordinates;

E) measuring the position and orientation of the first reference element at the bone or bone joint with respect to an on-site three-dimensional system of coordinates;

F) referencing the position and orientation of the plane of projection to the position and orientation of the first reference element in order to establish a mathematical relationship between the position and orientation of the plane of projection and the position and orientation of the bone or bone joint;

G) displacing the bone or bone joint in order to effect the desired surgical treatment at the bone or bone joint, whereby the surgical treatment may be e.g. a reduction manoeuvre;

H) measuring the actual position and orientation of the displaced bone or bone joint, whereby the actual position and orientation may be measured continuously during the surgical manoeuvre or subsequently;

I) determining the deviation between the actual position and orientation of the first reference element and the position and orientation of the first reference element referenced under step F);

K) determining the position of the C-arm X-ray device whereto the C-arm X-ray device has to be situated in order to reset the plane of projection as referenced under step F); and L) guiding the C-arm X-ray device in the new position and adjust the plane of projection as determined under step K) by means of automatic controlling means.

The measurement of the position and orientation of the reference elements with respect to the three-dimensional on-site system of coordinates is performed with a position measurement device that is connected to the computer using software to evaluate the coordinates from the data received from the position measurement device.

The reference bodies preferably comprise at least three markers that are non-collinearly arranged. The markers as well as the detectors of the position measurement device may be acoustic or electromagnetic effective means such as energy emitting, receiving or reflecting means. For instance as energy emitting means:

Light sources, particularly light emitting diodes (LED's);

Infrared light emitting diodes (IRED's); or

Acoustic transmitters or as energy receiving means:

Photodiodes; or

Microphones may be used. Other position measurement devices contain coils as energy emitting means and Hall-effect components as energy receiving means may be used as well.

A custom optoelectronic position measurement device may be used e.g. an OPTOTRAK 3020 System, Northern Digital, Waterloo, On., Canada. It preferably comprises an OPTOTRAK 3020 Position Sensor consisting of three one-dimensional charge-coupled devices (CCD) paired with three lens cells and mounted on a stabilised bar. Within each of the three lens cells, light from an infrared marker is directed onto a CCD and measured. All three measurements together determine—in real time—the three-dimensional location of the marker;

a system control unit;

a computer interface card and cables;

data collection and display software; and a strober and marker kit.

Computer assisted surgery systems (CAS systems) that are provided with a computer and a position measurement device in order to measure the position of surgical instruments or devices which are displaceable within the operation area are disclosed e.g. in U.S. Pat. No. 5,383,454 BUCH-HOLZ and EP 0 359 773 SCHLONDÖRFF. Often these CAS—systems comprise a memory means in order to store medical images such as e.g. X-rays, Computertomographs or MR images (Magnetic Resonance images) using radiant energy means. Thereby the medical images may be gathered pre-operatively or intraoperatively.

Additional advantageous embodiments of the invention are characterized in the subclaims.

The advantages achieved by the invention are essentially to be seen in the fact that, thanks to the method according to the invention shorter operation times;

reduced intraoperative radiation exposure; and reduction of personnel necessary during the surgical operation may be achieved.

Figure 2:
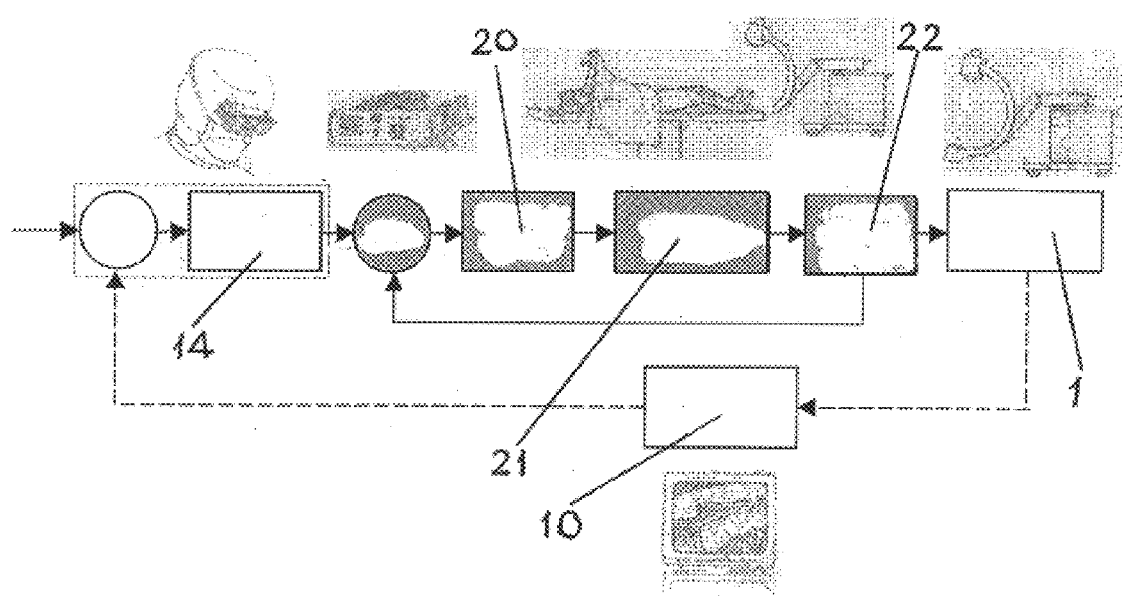
Figure 3:
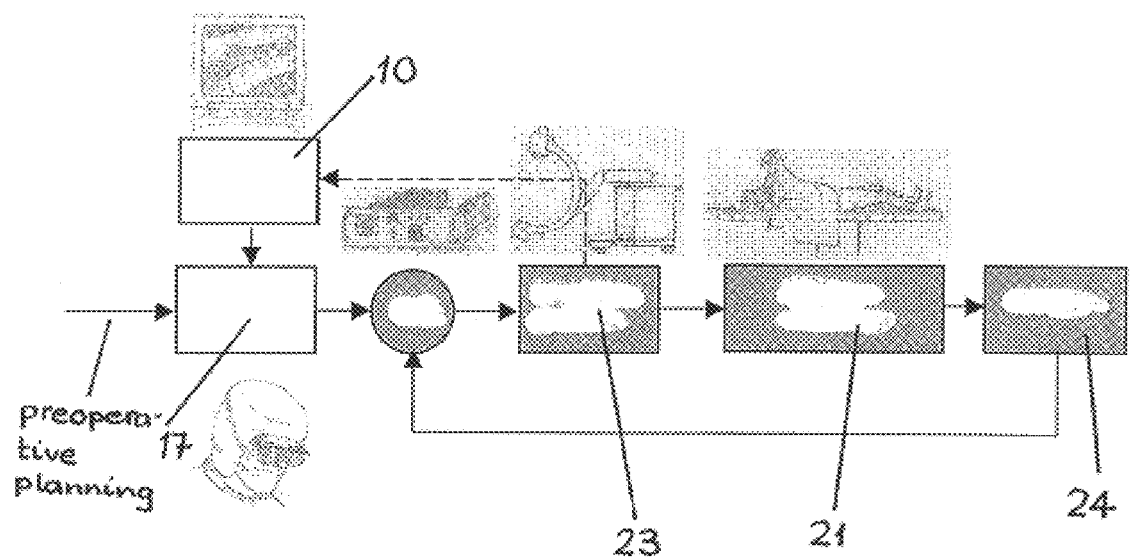

The invention and additional configurations of the invention are explained in even more detail with reference to the partially schematic illustration of several embodiments. Shown are:

FIG. 1 a perspective view of an operation room with a computer assisted surgery system, a C-arm X-ray device that is equipped with a reference element and a motorized exact positioning unit (MEPUC); and FIG. 2 a control circuit which is produced when the C-arm X-ray device is positioned for a projection for the first time, whereby a motorized exact positioning unit for the C-arm X-ray device is used; and FIG. 3 a control circuit which is produced when the combination of the C-arm X-ray device, a motorized exact positioning unit for the C-arm and a surgical navigation or computer assisted surgical system are used for positioning the C-arm X-ray device.

In FIG. 1 a C-arm X-ray device 1 is represented in connection with a computer assisted surgery system comprising a position measurement device 7 and a computer 9. The different steps of the method according to the invention are effected with these devices shown in FIG. 1 as follows:

A) the first reference element 3 is fixed at the bone 4 to be surgically treated. The fixation means to attach the first reference element 3 at the bone 4 may be a bone screw. The first reference element 3 is provided with three non-linearly arranged infrared light emitting diodes;

B) to position the C-arm X-ray device 1 in a position with a desired plane of projection 2 at the bone 4 or bone joint to be surgically treated the C-arm X-ray device may be manually or automatically actuated;

C) the position and orientation of the second reference element 6 at the C-arm X-ray device 1 is measured with respect to an on-site three-dimensional systems of coordinates 5 through measuring the positions of three non-linearly arranged markers 11 attached to the second reference element 6. The markers 11 may be Infrared light emitting diodes;

D) the determination of the position and orientation of the plane of projection 2 with respect to the on-site systems of coordinates 5 is effected by means of determining a coordinate transformation between the position and orientation of the second reference element 6 at the C-arm X-ray device 1 and the adjustment of the plane of projection 2 relative to this second reference element 6;

E) the measurement of the position and orientation of the first reference element 3 at the bone 4 with respect to an on-site three-dimensional system of coordinates 5 is performed by means of the position measurement device 7 and the computer 9 as well;

F) the referencing of the position and orientation of the plane of projection 2 to the position and orientation of the first reference element 3 is performed by means of the computer 9 whereby a mathematical relationship between the plane of projection 2 and the first reference element is established and stored in a data storage means of the computer 9;

G) the surgical treatment of the bone 4 including e.g. a displacement of the bone 4 may be performed with intraoperative and continuous use of the C-arm X-ray device 1 or with intraoperative discontinuous use of the C-arm X-ray device 1 whereby the latter is used only to verify the performed surgical treatment;

H) the measurement of the actual position and orientation of the first reference element 3 displaced with the bone 4 or bone joint is performed via the position measurement device 7 and the computer 9;

I) the determination of the deviation between the actual position and orientation of the first reference element 3 and the position and orientation of the first reference element 3 referenced under step F) is performed via the computer 9;

K) the new position of the C-arm X-ray device 1 in order to reset the plane of projection 2 as referenced under step F) is determined via the computer 9; and L) the guidance of the C-arm X-ray device 1 into the new position and adjustment of the plane of projection 2 as determined under step K) is performed by means of automatic controlling means directing the motorized exact positioning unit that displaces the C-arm into the desired position. When using a computer assisted surgery system as described here the automatic controlling means are preferably performed through software means effectable with the computer 9.

In case of using infrared light emitting diodes as markers 1 the position measurement device 7 is provided with cameras 8 that are preferably provided with CCD-chips (charge coupled devices).

FIG. 2 shows the control circuit which is produced when the C-arm is used to reproduce a projection for the first time with a motorized exact positioning unit (MEPUC) for setting the C-arm in a desired position. A serial connection of two control circuits is necessary to describe this process with this configuration. The MEPUC takes on the role of the C-arm operator and takes over the function of the controller in the inner control circuit. The regulatory behavior in this inner control circuit is improved since the positional directions of the surgeon are now translated into movements of the C-arm without interpretation on the part of the operator. The surgeon receives his visual feedback on the position attained directly: the surgeon's eyes function as the measuring unit for the inner control circuit. Visual feedback in the outer control circuit is produced by radiography (measuring unit: C-arm).

In contrast, the reproduction of a previously set projection with this constellation can be described by an optimized control circuit. Only the patient, the C-arm and the MEPUC are involved in the regulatory process which can be described by its own control circuit. The surgeon acts as the target value transmitter by selecting the projections to be reproduced. The positioning of the C-arm is then automatically MEPUC-controlled by the controller based on directional data previously entered. The surgeon decides whether he is satisfied with the result of positioning and whether he wishes to conclude the procedure with radiographic assessment.

In FIG. 2 the interpreter is referenced as 14, the drive of the MEPUC is referenced as 20, the patient as 21, the measuring system MEPUC as 22 and the C-arm X-ray device as 1.

FIG. 3 shows a regulatory process explaining the situation if MEPUC is used in combination with a surgical navigation system, the positional data from the C-arm and the targeted objects can serve as input values from which command signals are produced for the motors. Even with this combination, the initial setting for a projection can be described with the optimal control circuit. The surgeon acts as target value transmitter by defining the required relative positions for the desired projection as described above. At the same time, the current positional data for the C-arm and the targeted object are available at the input to the MEPUC. The MEPUC controller calculates the control deviation and generates its own commands to the motors by which the current actual position is converted into the target position. In this configuration, the surgical navigation system is integrated as a measuring unit (to determine position) into the control circuit which positions the C-arm.

For the reproduction of a projection with this version of the MEPUC, positional data from fragments and the C-arm are stored after the first successful positioning attempt. These data serve as target values for the MEPUC during the reproduction of a projection once the surgeon has selected the projection to be reproduced. The actual positions are recorded by the navigation system as a measuring unit and the deviation is again calculated by the MEPUC controller. Since the surgical navigation system always measures relative positions, the fragments can be moved at will in relation to each other without affecting the reproduction precision of the projection, e.g. during a reduction manoeuvre.

In FIG. 3 the surgeon is referenced as 17, the C-arm X-ray device including the MEPUC is referenced as 23, the patient as 21 and the surgical navigation system as 24.

What is claimed is:

1. Method of automatically guiding a C-arm X-ray device which is equipped with a motorized exact positioning unit comprising the steps of:
    (A) attaching a first reference element (3) at a bone (4) or bone joint to be surgically treated;
    (B) positioning the C-arm X-ray device (1) in a desired position with a desired plane of projection (2) at the bone (4) or bone joint to be surgically treated;
    (C) measuring a position and orientation of a second reference element (6) at the C-arm X-ray device (1) with respect to an on-site three-dimensional system of coordinates (5);
    (D) determining a position and orientation of the plane of projection (2) with respect to the on-site system of coordinates (5);
    (E) measuring a position and orientation of the first reference element (3) at the bone (4) or bone joint with respect to the on-site three-dimensional system of coordinates (5);
    (F) referencing the position and orientation of the plane of projection (2) to the position and orientation of the first reference element (3); and
    (G) displacing the bone (4) or bone joint in order to effect a desired surgical treatment at the bone (4) or bone joint, characterized in that the method further comprises the steps of:
    (H) measuring an actual position and orientation of the displaced bone (4) or bone joint;
    (I) determining a deviation between the actual position and orientation of the first reference element (3) and the position and orientation of the first reference element (3) referenced under step (F);
    (J) determining a new position of the C-arm X-ray device (1) in order to reset the plane of projection (2) as referenced under step (F); and
    (K) guiding the C-arm X-ray device (1) in the new position and adjusting the plane of projection (2) as determined under step (J) by means of an automatic controlling means.

2. Method according to claim 1, characterized in that it further comprises the step of storing at least one position and orientation of the bone (4) or bone joint as well as at least one position and orientation of the plane of projection (2) as sets of binary data in a data storage means of the computer (9).

3. Method according to claim 2, wherein the method further comprises the steps of:
    (A) recalling the sets of binary data stored in a data storage means of the computer (9) and loading the sets of binary data into the central processing unit of the computer (9); and
    (B) displacing the C-arm X-ray device (1) into the position of the stored position and orientation of the plane of projection (2) through processing of the data recalled under step (A).

4. Method according to claim 1, wherein the automatic controlling means are integrated within the C-arm X-ray device (1) as an integrated controller.

5. Method according to claim 1. wherein the automatic controlling means are performed through software means effectable with the computer (9).

6. Method according to claim 2, wherein the automatic controlling means are integrated within the C-arm X-ray device (1) as an integrated controller.

7. Method according to claim 3, wherein the automatic controlling means are integrated within the C-arm X-ray device (1) as an integrated controller.

8. Method according to claim 2, wherein the automatic controlling means are performed through software means effectable with the computer (9).

9. Method according to claim 3, wherein the automatic controlling means are performed through software means effectable with the computer (9).

* * * * *

UNITED STATES PATENT AND TRADEMARK OFFICE
CERTIFICATE OF CORRECTION

PATENT NO. : 6,491,429 B1
DATED : December 10, 2002
INVENTOR(S) : Suhm

It is certified that error appears in the above-identified patent and that said Letters Patent is hereby corrected as shown below:

Column 1,
Line 3, before Line 4, insert the centered heading -- BACKGROUND OF THE INVENTION --.
Line 5, delete "according to the concept of claim 1".
Line 41, after "system." delete "Intraoperative imaging with the C-arm"

Column 2,
Line 25, after "projection." delete "Intraoperative imaging with the combination C-arm/ Surgical Navigation System".

Column 3,
Line 14, delete "manoeuvre" and insert -- maneuver --.
Line 26, after "manipulations." insert the centered heading -- SUMMARY OF THE INVENTION --.
Line 31, after "means." delete "The invention solves the posed problem with a method that displays the features of claim 1."

Column 4,
Lines 10 and 14, delete "manoeuvre" and insert -- maneuver --.
Line 20, delete "K)" and insert -- J) --.
Line 24, delete "L)" and insert -- K) --.
Line 53, delete "charge-coupled" and insert -- chargecoupled --.

Column 5,
Line 7, after "intraoperatively.", delete "Additional advantageous embodiments of the invention are characterized in the subclaims.".
Line 16, after "achieved.", insert the centered heading -- BRIEF DESCRIPTION OF THE DRAWINGS --.
Line 20, delete "Shown are:" and insert -- wherein: --.
Line 33, after "device.", insert the centered heading -- DETAILED DESCRIPTION OF THE PREFERRED EMBODIMENTS --.
Line 36, after "9", insert -- and a display 10 --.

UNITED STATES PATENT AND TRADEMARK OFFICE
CERTIFICATE OF CORRECTION

PATENT NO.    : 6,491,429 B1
DATED         : December 10, 2002
INVENTOR(S)   : Suhm It is certified that error appears in the above-identified patent and that said Letters Patent is hereby corrected as shown below:

Column 6,
Line 24, delete "K)" and insert -- J) --.
Line 27, delete "L)" and insert -- K) --.
Line 29, delete "K" and insert -- J --.
Line 37, delete "1" and insert -- 11 --.

Signed and Sealed this

Tenth Day of June, 2003

JAMES E. ROGAN
*Director of the United States Patent and Trademark Office*